(12) United States Patent
Wei et al.

(10) Patent No.: US 11,884,706 B2
(45) Date of Patent: Jan. 30, 2024

(54) IMMUNOMODULATING PEPTIDE DERIVED FROM CONCAVE-EARED TORRENT FROG AND USE THEREOF

(71) Applicant: SOOCHOW UNIVERSITY, Suzhou (CN)

(72) Inventors: Lin Wei, Suzhou (CN); Yang Yang, Suzhou (CN); Wei Xu, Suzhou (CN)

(73) Assignee: SOOCHOW UNIVERSITY, Suzhou (CN)

( * ) Notice: Subject to any disclaimer, the term of this patent is extended or adjusted under 35 U.S.C. 154(b) by 309 days.

(21) Appl. No.: 17/299,472

(22) PCT Filed: Aug. 7, 2020

(86) PCT No.: PCT/CN2020/107720
§ 371 (c)(1),
(2) Date: Jun. 3, 2021

(87) PCT Pub. No.: WO2021/057279
PCT Pub. Date: Apr. 1, 2021

(65) Prior Publication Data
US 2022/0024998 A1 Jan. 27, 2022

(30) Foreign Application Priority Data

Sep. 29, 2019 (CN) .......................... 201910935233.3

(51) Int. Cl.
*C07K 14/46* (2006.01)
*A61P 17/02* (2006.01)
*A61K 38/00* (2006.01)

(52) U.S. Cl.
CPC ............ *C07K 14/463* (2013.01); *A61P 17/02* (2018.01); *A61K 38/00* (2013.01)

(58) Field of Classification Search
CPC ....... C07K 14/463; A61P 17/02; A61K 38/00; A61Q 19/00
See application file for complete search history.

(56) References Cited

U.S. PATENT DOCUMENTS

2018/0271938 A1  9/2018  Bancel et al.

FOREIGN PATENT DOCUMENTS

| CN | 101333258 A | 12/2008 |
| CN | 102657845 A | 9/2012 |
| CN | 110577588 A | 12/2019 |

OTHER PUBLICATIONS

Uniprot Protein Database, Protein Accession A0A5J6BS14, accessed on Jun. 2, 2023, WHP protein.*
He et al. "A Frog-Derived Immunomodulatory Peptide Promotes Cutaneous Wound Healing by Regulating Cellular Response" Frontiers in Immunology, vol. 10, Articles 2421, pp. 1-20 (Oct. 17, 2019).
GenBank Accession No. QEG59350.1 "WHP precursor [Odorrana tormota]" GenBank, Oct. 15, 2019.
Miao et al. "Study on effect of antimicrobial peptides Dybowskin-1st from skin of Rana dybowskii on wound healing skin of mice" Chinese Journal of Experimental Traditional Medical Formulae, vol. 17, No. 23, pp. 125-128 (Dec. 5, 2011).

* cited by examiner

*Primary Examiner* — Julie Ha
*Assistant Examiner* — Erinne R Dabkowski
(74) *Attorney, Agent, or Firm* — SZDC Law PC

(57) ABSTRACT

The present invention relates to an immunomodulating peptide comprising an amino acid sequence as shown in SEQ ID NO:1. The present invention also discloses use of the immunomodulating peptide in the preparation of a drug or skin care product for promoting skin wound healing. The present invention provides a new immunomodulating peptide and use thereof, and discloses the mechanism of action of the immunomodulating peptide in promoting wound healing. The immunomodulating peptide is useful as a wounding healing polypeptide template.

8 Claims, 9 Drawing Sheets

Specification includes a Sequence Listing.

SEQUENCE LISTING

```
<160> NUMBER OF SEQ ID NOS: 2

<210> SEQ ID NO 1
<211> LENGTH: 24
<212> TYPE: PRT
<213> ORGANISM: Odorrana tormota
<220> FEATURE:
<223> OTHER INFORMATION: Ot-WHP Peptide

<400> SEQUENCE: 1

Ala Thr Ala Trp Asp Leu Gly Pro His Gly Ile Arg Pro Leu Arg Pro
1               5                   10                  15

Ile Arg Ile Arg Pro Leu Cys Gly
            20
```

-continued

```
<210> SEQ ID NO 2
<211> LENGTH: 24
<212> TYPE: PRT
<213> ORGANISM: Artificial Sequence
<220> FEATURE:
<223> OTHER INFORMATION: Scrambled Ot-WHP Peptide

<400> SEQUENCE: 2

Pro Gly Pro Ile Pro Ala His Leu Gly Arg Arg Trp Ala Ile Leu Ile
1               5                   10                  15

Arg Pro Asp Leu Thr Arg Cys Gly
            20
```

IMMUNOMODULATING PEPTIDE DERIVED FROM CONCAVE-EARED TORRENT FROG AND USE THEREOF

This application is the National Stage Application of PCT/CN2020/107720, filed on Aug. 7, 2020, which claims priority to Chinese Patent Application No. 201910935233.3, filed on Sep. 29, 2019, which is incorporated by reference for all purposes as if fully set forth herein.

FIELD OF THE INVENTION

The present invention relates to the technical field of medical molecular biology, and more particularly to an immunomodulating peptide derived from concave-eared torrent frog and use thereof.

DESCRIPTION OF THE RELATED ART

Wound healing is a general term for the pathological process occurring after skin infection or physical trauma, and is a highly ordered biological process in which various types of cells restore the tissue integrity. The wound healing process involves several different types of cells, and the cell activity of any particular cell type may change in different stages of repair. The complexity and coordination of the healing process are main obstacles in the treatments, so any therapeutic agent needs to effectively arranged in an appropriate stage. As a normal biological process in the human body, wound healing is achieved by means of four precise and highly programmed stages including hemostasis, inflammation, proliferation and remodeling. Wound healing is a dynamic process. The interruption, abnormality or extension of the process at each stage may lead to delayed or non-healing chronic wounds. Poor wound healing or wound disruption is a common symptom after surgery, which results in a variety of poor prognosis, including wound infection and scar formation. Many postoperative infections cause hard-to-heal wounds, which bring great pain and psychological burden to patients.

In the past ten years, treatments with various new biological agents have achieved certain results. At present, the effective drugs that can promote wound healing mainly are growth factors, including epidermal growth factor (EGF), fibroblast growth factor-2 (FGF-2), vascular endothelial growth factor (VEGF), platelet-derived growth factor (PDGF), keratinocyte growth factor-1 (KGF-1), granulocyte macrophage colony stimulating factor (GM-CSF), granulocyte colony stimulating factor (G-CSF) and the like. Although treatments based on these growth factors have found some use in clinic, the large molecular weights and high production costs of these growth factors limit its use in clinic.

The skin of amphibians is an effective natural barrier and plays an important role in defense, respiration and moisture regulation. Due to the complex living environment, the skin of amphibians is often damaged by various biological and non-biological injuries, for example, predation, parasitic infection, microbial infection and some physical injuries. However, surprisingly the skin of amphibians has good healing ability even without any post-injury care. This shows that amphibians have developed excellent healing systems, and wound healing peptides are an important component involved therein. Although some amphibian-derived wound healing peptides have been reported, such as the antibacterial peptides disclosed in CN201510000510.3 and CN201810366376.2, the mechanisms of action of the healing peptides have not been thoroughly studied, such as the chemotaxis effect on neutrophils in the wound, whether the healing peptides have direct chemotactic effects on neutrophils and macrophages, and the regulating effect between effector cells.

Concave-eared torrent frog is mostly distributed in Huangshan Mountain, Anhui Province, China. It hides in dark and humid caves during the day, and often preys on shrubs, short grass branches or grass leaves on both sides of mountain streams at night. Because of its concaved tympanic membrane and slightly forward-sloped external auditory canal, scientists have mostly focused on its ultrasound communication and behavioral studies using ultrasound communication. There is no report of biologically active peptides.

SUMMARY OF THE INVENTION

To solve the above technical problems, an object of the present invention is to provide an immunomodulating peptide derived from a concave-eared torrent frog and use thereof. The present invention provides a new immunomodulating peptide and use thereof. The immunomodulating peptide can be used as a novel wound healing polypeptide template.

A first object of the present invention is to disclose an immunomodulating peptide (hereinafter referred to as Ot-WHP) having an amino acid sequence as shown in SEQ ID NO:1. Ot-WHP is composed of 24 amino acids and has a molecular weight of 2666.19 Daltons.

Preferably, the immunomodulating peptide is derived from concave-eared torrent frog (Latin name *Odorrana tormota*).

Preferably, the immunomodulating peptide is derived from the skin of concave-eared torrent frog.

A second object of the present invention is to disclose use of the immunomodulating peptide in the preparation of a drug or a skin care product for promoting skin wound healing.

Preferably, the drug is used to promote the healing of human skin wounds.

Preferably, in the presence of macrophages, the drug causes the migration of neutrophils and macrophages.

Preferably, the drug induces the mouse macrophages and skin wounds to produce chemokines and cytokines.

Preferably, the drug activates the MAPKs, NF-κB and TGF-β/Smad signaling pathways in bone marrow-derived macrophages.

Preferably, in the presence of macrophages, the drug promotes the proliferation of keratinocytes and fibroblasts.

Preferably, in the presence of macrophages, the drug promotes the transformation of fibroblasts into fibrocytes and promotes the collagen production by fibroblasts.

Preferably, in the presence of macrophages, the concentration of immunomodulating peptide in the drug is 20-100 µg/mL.

By means of the above technical solutions, the present invention has the following advantages.

The present invention provides a new immunomodulating peptide Ot-WHP, which has a small molecular weight and a low production cost. When used in the preparation of drugs for promoting skin wound healing, the immunomodulating peptide has broad application prospect and clear mechanism of action, and can be used as a novel wounding healing polypeptide template in the future.

Ot-WHP of the present invention can significantly promote wound healing in mice. Moreover, Ot-WHP has a small molecular weight, a simple structure, and is easy for chemical synthesis and protein expression. Ot-WHP has a clear mechanism of action. These advantages make it a new generation of excellent candidate polypeptide for clinically promoting wound healing.

The above description is only a summary of the technical solutions of the present invention. To make the technical means of the present invention clearer and implementable in accordance with the disclosure of the specification, the preferred embodiments of the present invention will be described in detail with reference to the accompanying drawings.

DETAILED DESCRIPTION OF THE PREFERRED EMBODIMENTS

Figure 1:
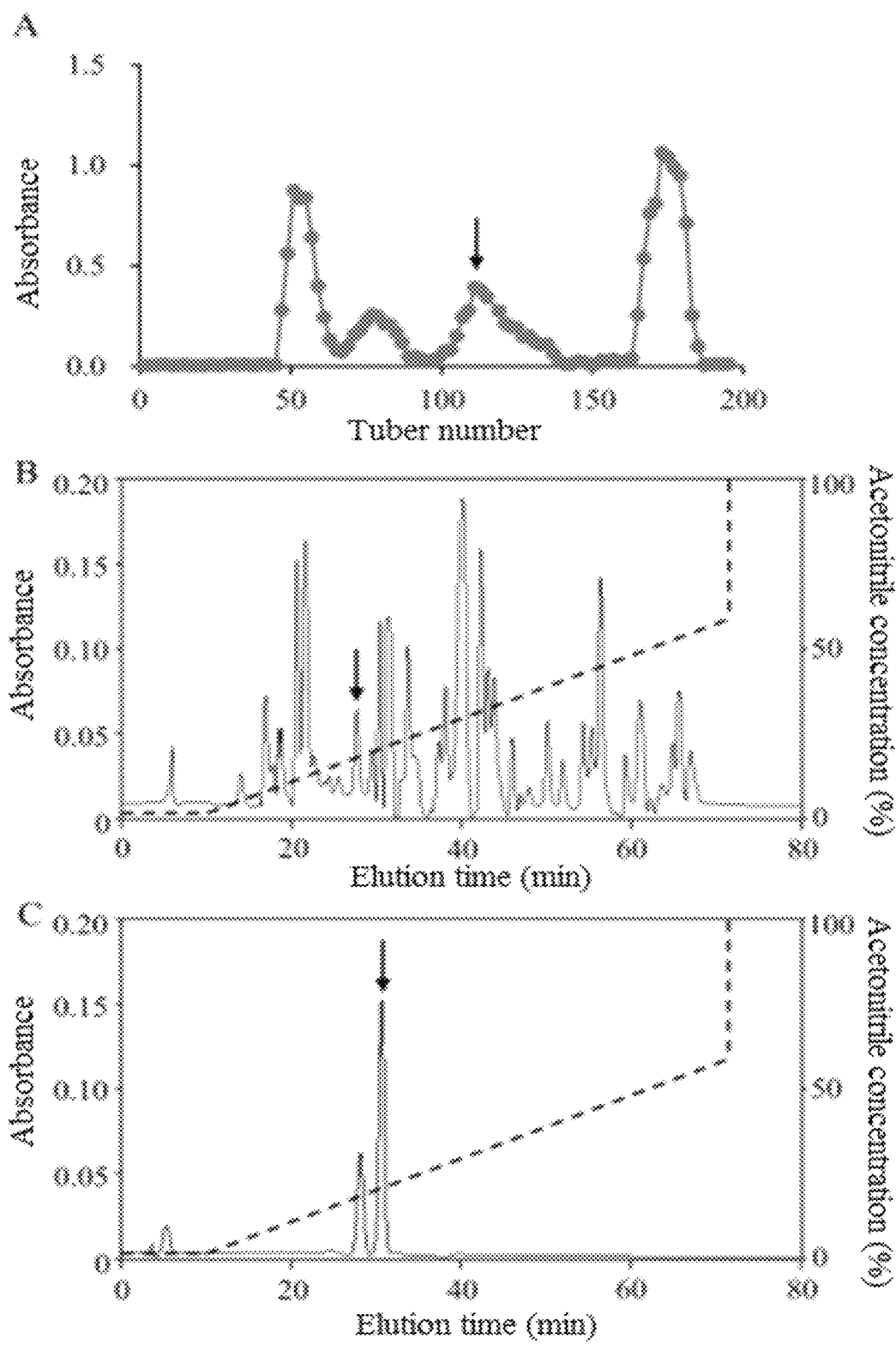
FIG. 1 illustrates the active peak obtained at a wavelength of 280 nm in the process of separating and preparing Ot-WHP from the skin secretion of concave-eared torrent frog in Example 1.

The specific embodiments of the present invention will be described in further detail with reference to embodiments. The following embodiments are intended to illustrate the present invention, instead of limiting the scope of the present invention.

EXAMPLE 1

Separation and Preparation of Ot-WHP From the Skin Secretion of Concave-Eared Torrent Frog The concave-eared torrent frogs were collected from Huangshan Mountain, China. The concave-eared torrent frog was stimulated with a small amount of ether, and a large amount of secretion was produced on the back of the frog body. The secretion was collected, and centrifuged at 5000×g for 10 min. The supernatant was collected and lyophilized. The lyophilized powder was dissolved in 10 mL of PBS (0.1 M, pH 6.0) and centrifuged at 5000×g for 10 min. The supernatant was collected and loaded onto Sephadex G-50 (Superfine, Amersham Biosciences, 2.6 cm×100 cm) gel chromatographic column, and subjected to filtration chromatography with a PBS buffer (0.1 M, pH 6.0). The eluate was collected every 10 minutes in 3 mL each tube, and about 200 tubes were collected. After the collection, the absorbency of each tube at 280 nm was detected, and FIG. 1A was plotted according to the absorbency of each tube.

According to FIG. 1A, the skin secretion of concave-eared torrent frog was roughly divided into four absorption peaks after filtration chromatography by Sephadex G-50 gel. Each peak was combined, and whether each peak has the activity of promoting skin wound healing in mice was detected according to Example 3. One peak is found to have the function of promoting skin wound healing in mice (shown by the arrow in FIG. 1A). Then active peak in FIG. 1A was loaded onto a C18 (5 µm particle size, 110 Å pore size, 250 mm×4.6 mm, Gemini, CA, USA) reverse-phase high-performance liquid chromatographic column equilibrated with 0.1% trifluoroactic acid in water, and subjected to filtration chromatography eluting with acetonitrile over 0-60% gradient. The elution time was 80 min, and the absorbency at 280 nm was detected. The light absorption characteristics are shown in FIG. 1B. As described above, the activity to promote the repair of skin wounds was traced. The active peak in FIG. 1B is marked with an arrow. Next, under the same conditions as in FIG. 1B, the active peak in FIG. 1B was subjected to a second filtration chromatography by a reverse-phase high-performance liquid chromatographic column. The result is shown in FIG. 1C. The active peak is marked with an arrow and named Ot-WHP.

EXAMPLE 2

Amino Acid Sequencing of Ot-WHP

The Ot-WHP purified in Example 1 was loaded onto the Shimadzu protein pulse liquid sequencer (PPSQ-31A; Shimadzu, Kyoto, Japan), followed by Edman degradation sequencing following the instruction of instrument. After sequencing, the amino acid sequence is ATAWDLGPHGIRPLRPIRIRPLCG (SEQ ID NO:1).

In a practical application process, Ot-WHP can be directly chemically synthesized according to the known amino acid sequence of Ot-WHP.

EXAMPLE 3

Ot-WHP Can Significantly Promote Skin Wound Healing in Mice

Experimental animals BALB/c mice, female, 6-8 weeks old, weighed 18-20 g, were purchased from Shanghai Slac Animal Co., Ltd. The mice were anesthetized by intraperitoneal injection of 2% sodium pentobarbital (0.1 mL/20 g), and the back was shaved with an electric razor and disinfected with iodophor. A hole was punched in the exposed back by a biopsy punch having a diameter of 8 mm. After the operation, the mice were kept in separate cages until the end of the experiment. The mice were randomly divided into 6 groups having 5 animals in each group, including a negative control group (20 µL PBS), a natural Ot-WHP group (20 µL, 200 µg/mL), a synthetic Ot-WHP group (20 µL, 200 µg/mL), a scrambled Ot-WHP group (SEQ ID NO:2, 20 µL, 200 µg/mL), an AH90 positive polypeptide control group (20 µL, 200 µg/mL), and an EGF growth factor control group (20 µL, 100 µg/mL). The drugs were dripped into corresponding wounds in mice once a day for 8 days.

Figure 2:
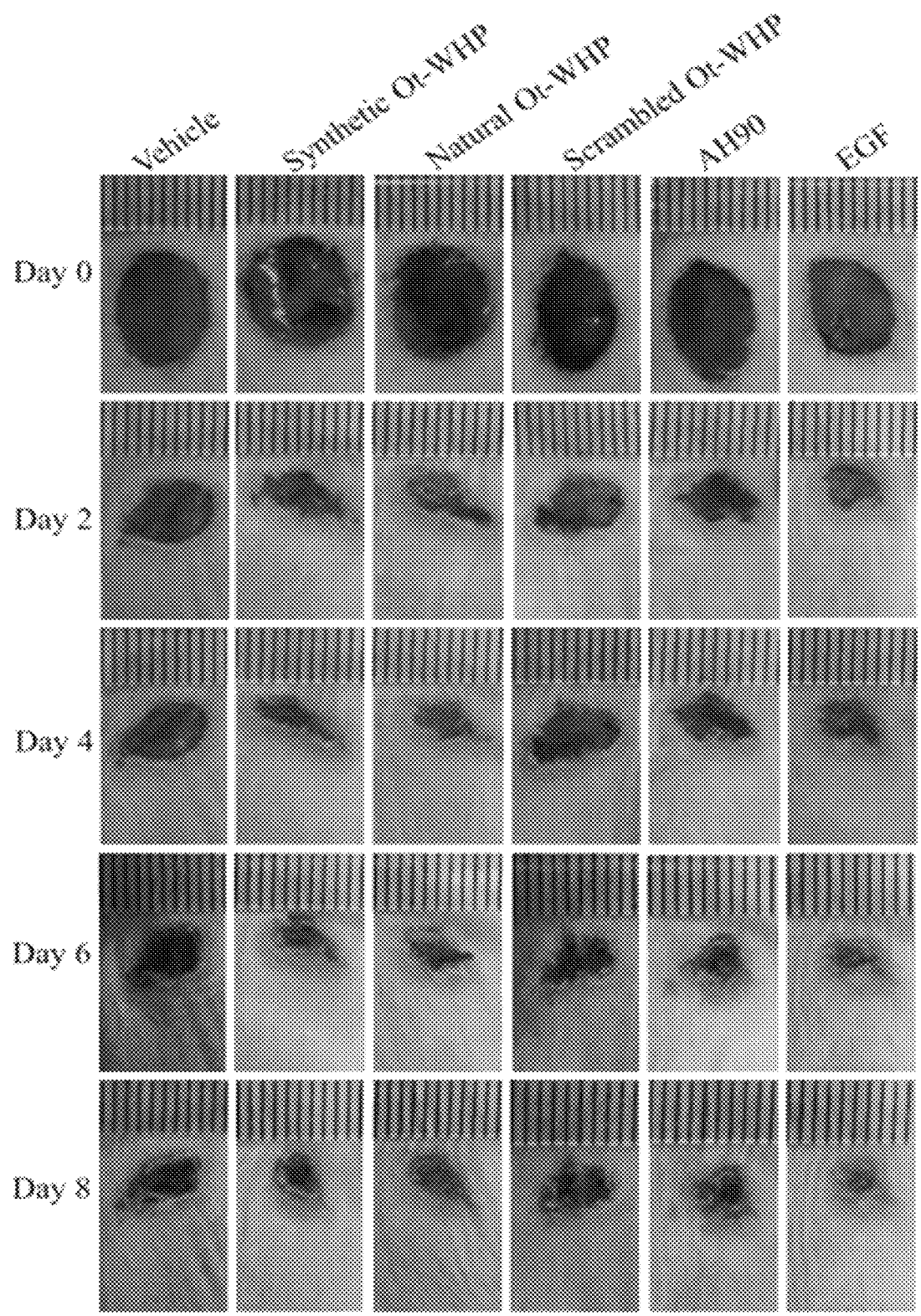
FIG. 2 is a photograph showing the skin wound healing of mice in different experimental groups in Example 3.
Figure 3:
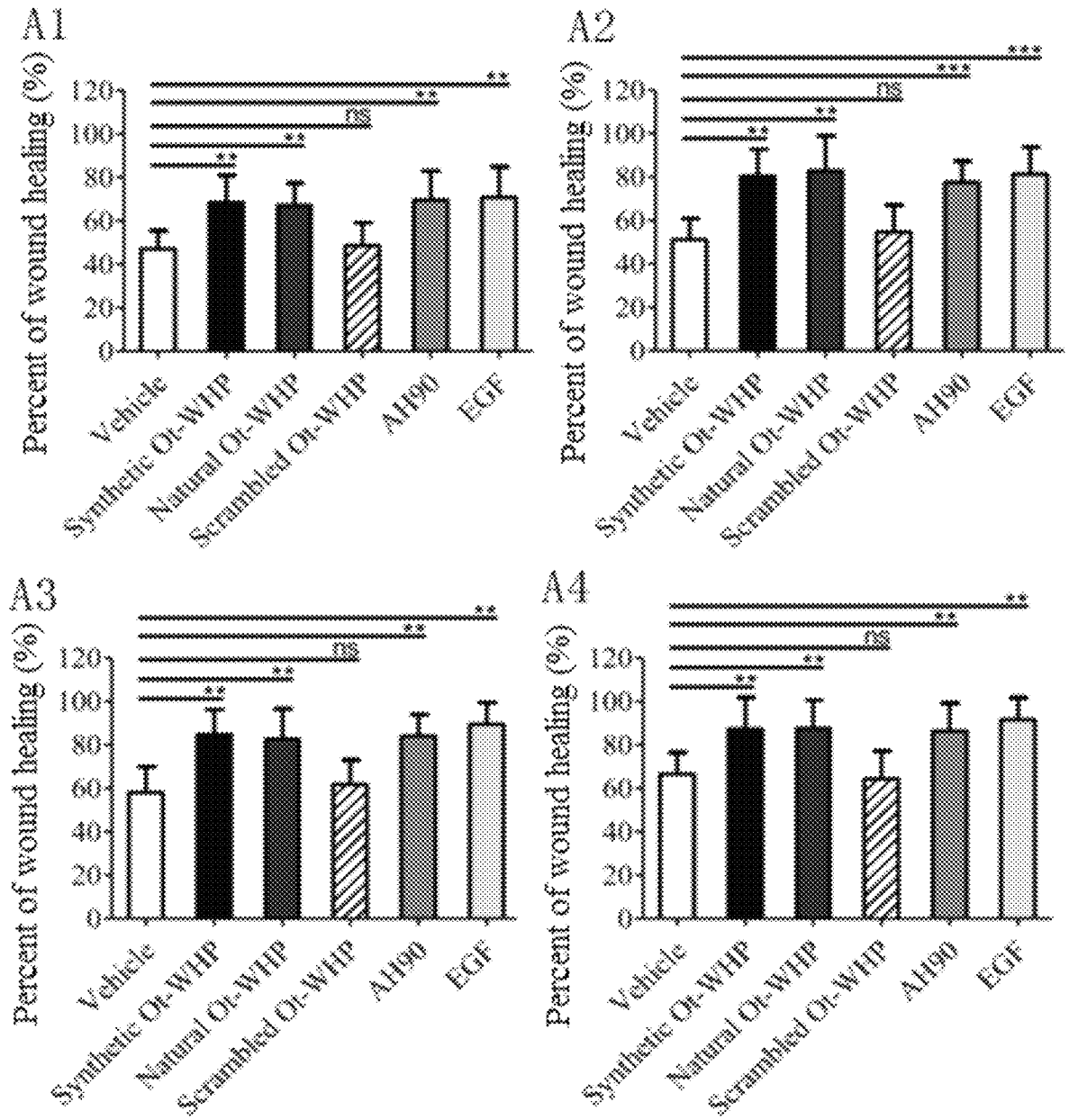
FIG. 3 shows the test results of skin wound healing rate of mice in different experimental groups in Example 3.

The results are shown in FIGS. 2-3. FIG. 2 shows the wound healing of mice in different experimental groups taken at 0, 2, 4, 6, and 8 days after operation. FIGS. 3A1-A4 show the wound healing rate of mice in different experimental groups at 2, 4, 6, and 8 days after surgery. In the figures, Vehicle represents the negative control group; synthetic Ot-WHP represents the synthetic Ot-WHP group; Natural Ot-WHP represents the natural Ot-WHP group; and Scrambled Ot-WHP represents the scrambled Ot-WHP group. The results show that both natural Ot-WHP and synthetic Ot-WHP can significantly promote the healing of mouse skin wounds with an effect comparable to AH90 and EGF, while the scrambled Ot-WHP has no activity to promote wound repair.

EXAMPLE 4

Ot-WHP Recruits Neutrophils and Macrophages to Migrate to the Wound, to Accelerate the Initial Stage of Inflammation in Wound Healing The mice were treated according to the method in Example 3. The drugs in the negative control group and the natural Ot-WHP group were dripped to wounds of corresponding mice. At specified time point (0.5, 1, 2, 3 days) after the operation, the mice were sacrificed. A biopsy tissue containing the wound center was taken, immobilized with 10% formalin, then dehydrated by ethanol, washed with xylene, and finally embedded in paraffin. The paraffin block was cut into 5 μm slices, deparaffinized, and hydrated, and antigen retrieval was performed for immunohistochemical analysis. The slice was blocked with 5% BSA for non-specific sites, incubated with the primary antibody (anti-Ly6G for neutrophils, and anti-F4/80 for macrophages) at 4° C., and immunostained with horseradish peroxidase and DBA. The infiltration by neutrophils and macrophages was measured by statistically counting the immunostained anti-Ly6G and anti-F4/80 cells.

Figure 4:
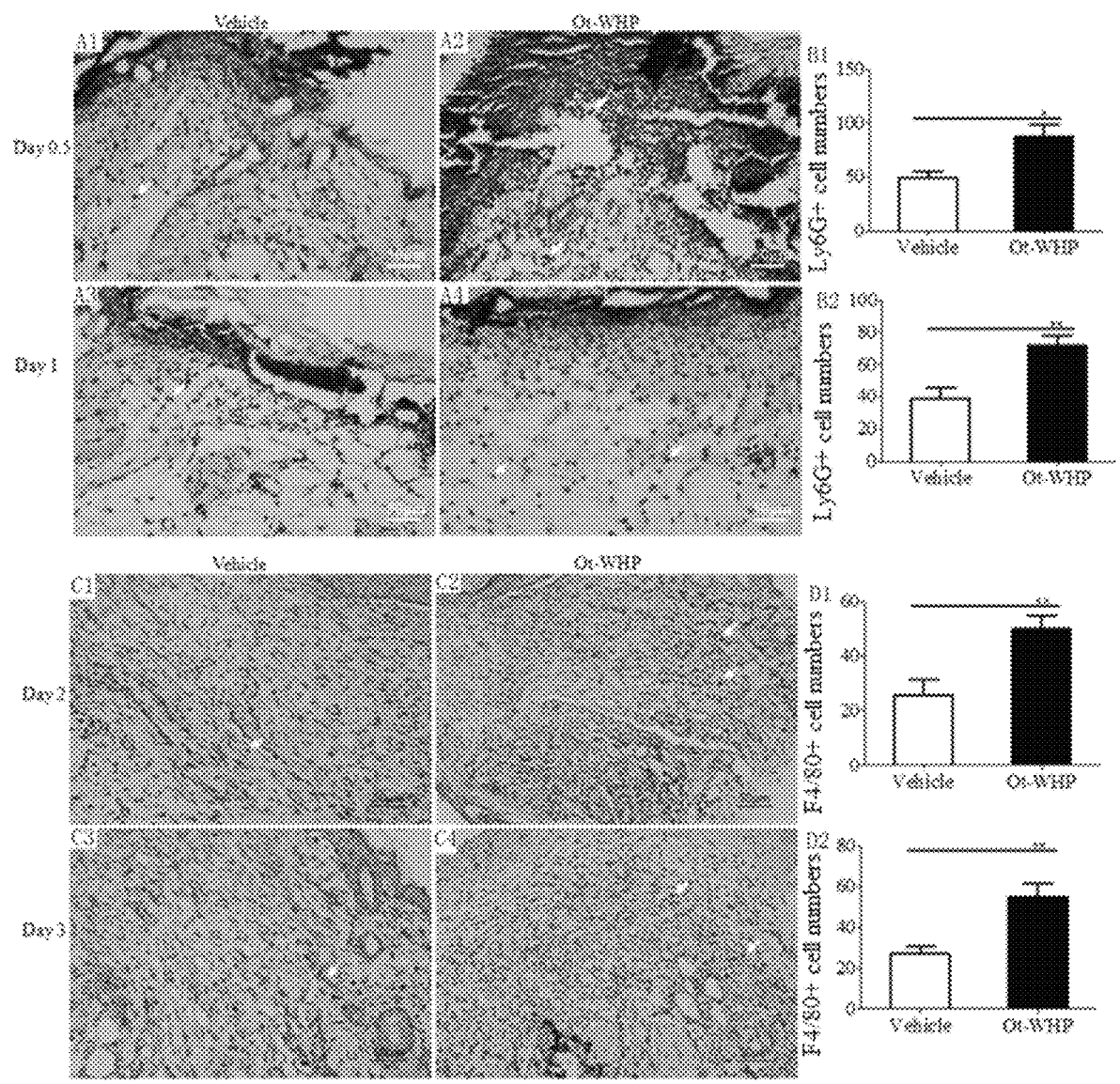
FIG. 4 shows the immunohistochemical and quantitative statistical results of neutrophils and macrophages of mice in different experimental groups in Example 4.

The results are shown in FIG. 4. FIGS. 4A1-A4 show the immunohistochemical results of neutrophils recruited on days 0.5 and 1 after operation of mice in different groups. FIGS. 4C1-C4 show the immunohistochemical results of macrophages recruited on days 2 and 3 after operation of mice in different groups. FIGS. 4B1-B2 show the statistical results of neutrophils recruited on days 0.5 and 1 after operation of mice in different groups. FIGS. 4D1-D2 show the statistical results of macrophages recruited on days 2 and 3 after operation of mice in different groups. The results show that Ot-WHP can promote the migration of neutrophils and macrophages to the wound.

EXAMPLE 5

Ot-WHP Does Not Directly Cause the Migration of Neutrophils and Macrophages, But Requires the Coexistence of Macrophages to Cause the Migration of Neutrophils and Macrophages To clarify how Ot-WHP chemoattracts neutrophils and macrophages to the wound area, the prepared mouse neutrophils or bone marrow-derived macrophages (BMDMs) were resuspended in RPMI 1640 medium containing 2% FBS at a cell density of $7 \times 10^6$ cells/mL. 100 μL was pipetted to a Transwell chamber with a pore size of 3.0 μm (upper chamber, 24-well plate). Then 500 μL of Ot-WHP (25, 50, 100 μg/mL, dissolved in RPMI 1640 medium containing 2% FBS) or the culture medium (control) was pipetted to the lower chamber, and then cultured in a cell incubator at 37° C. for 8 h. The cells in the lower chamber were collected and counted with a hemocytometer.

Figure 5:
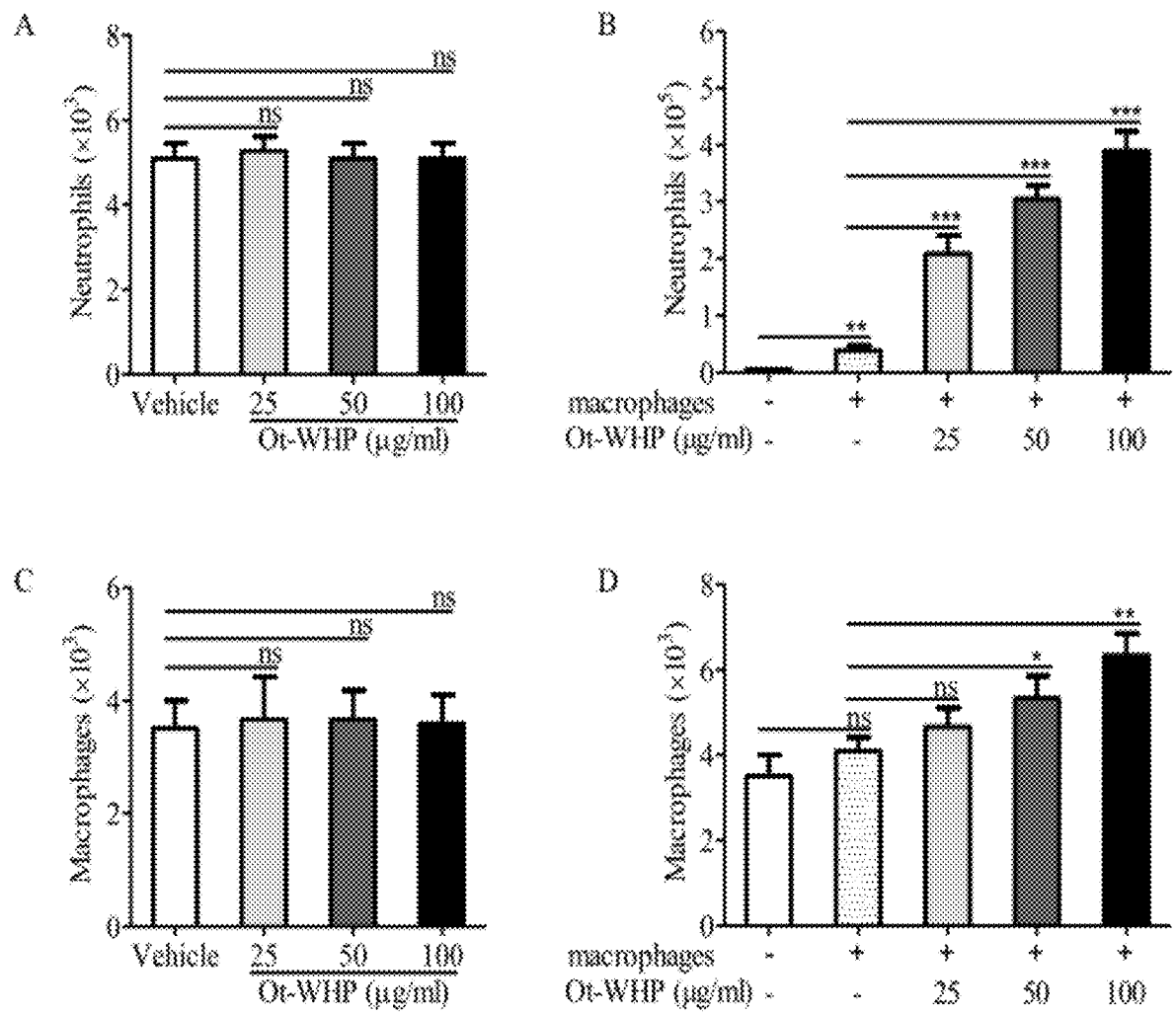
FIG. 5 shows the influence of Ot-WHP at different concentrations on the migration of neutrophils and macrophages in Example 5.

In a co-incubation system, mouse bone marrow-derived macrophages (BMDMs, $4 \times 10^6$ cells/mL, 500 μL) resuspended in in RPMI 1640 medium containing 2% FBS were plated in the lower chamber (24-well plate) of the co-incubation chamber. After adherence, the prepared mouse neutrophils ($7 \times 10^6$ cells/mL, 100 μL) or bone marrow-derived macrophages (BMDMs, $7 \times 10^6$ cells/mL, 100 μL) were added to the Transwell chamber with a pore size of 3.0 μm (upper chamber, 24-well plate). Then 500 μL of Ot-WHP (25, 50, 100 μg/mL, dissolved in RPMI 1640 medium containing 2% FBS) or the culture medium (control) was added to the lower chamber, and then cultured in a cell incubator at 37° C. for 8 h. The cells in the upper chamber were collected and counted with a hemocytometer. The reduced cells in the upper chamber are the migrated cells The results are shown in FIG. 5. Ot-WHP does not directly cause the migration of neutrophils (FIG. 5A) and macrophages (FIG. 5C) at a concentration in the range of 25-100 μg/mL. However, when macrophages coexist, Ot-WHP at a concentration in the range of 25-100 μg/mL significantly causes the migration of neutrophils (FIG. 5B) and macrophages (FIG. 5D) in a dose-dependent manner.

EXAMPLE 6

Ot-WHP Can Induce Mouse Macrophages and Skin Wounds to Produce Chemokines and Cytokines To clarify why Ot-WHP can cause the migration of neutrophils and macrophages in the coexistence of macrophages, mouse bone marrow-derived macrophages (BMDMs, $5 \times 10^5$ cells/well, DMEM medium, 2% FBS) were plated in a 24-well plate, Ot-WHP (25, 50, 100 μg/mL) or an equal volume of PBS (Vehicle) were added, and cultured for 24 h. The supernatant was collected, and centrifuged at 10000×g for 10 min. The chemokines and cytokines were determined.

Figure 6:
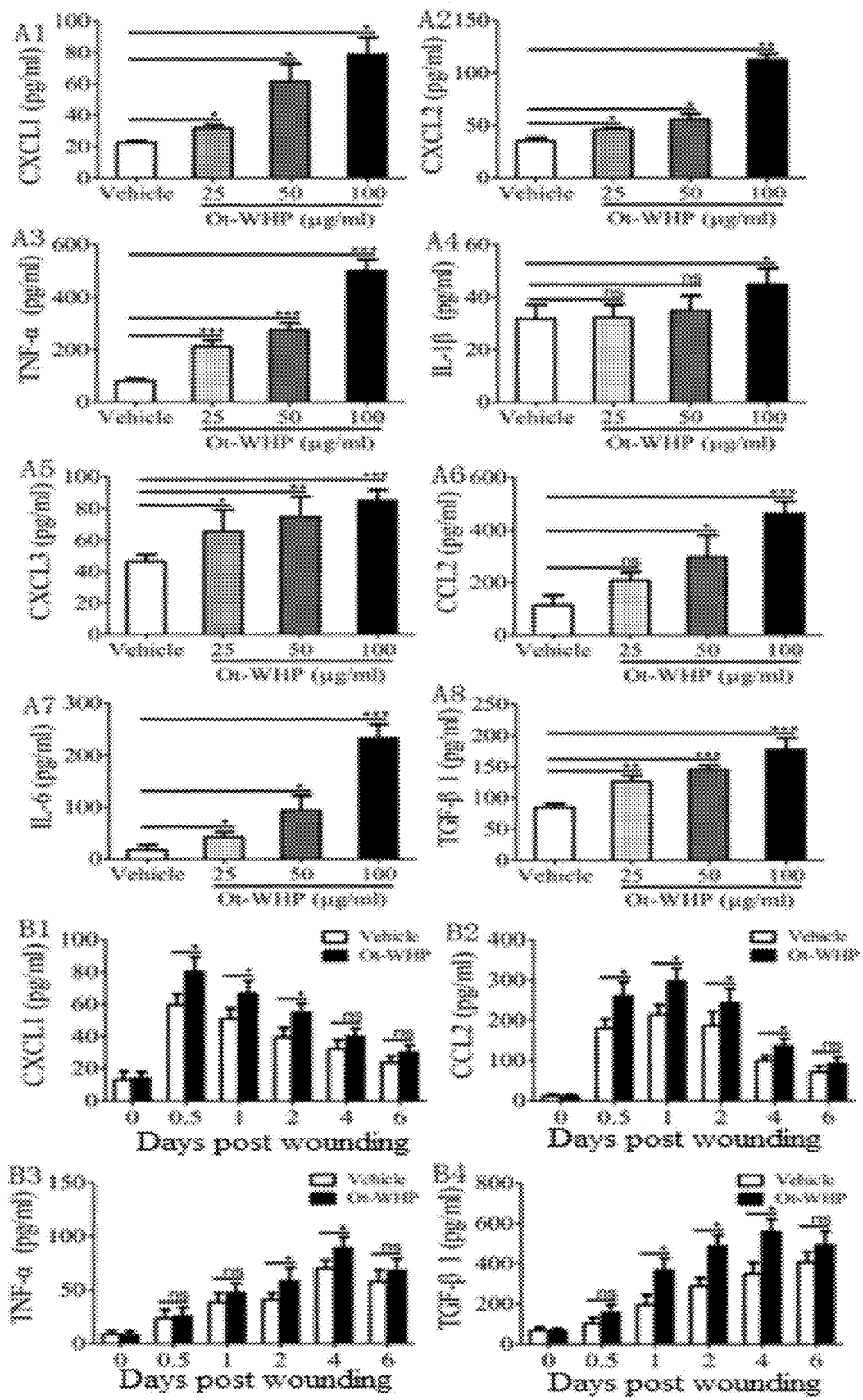
FIG. 6 shows the effect of Ot-WHP at different concentrations on the production of chemokines and cytokines in mouse BMDMs cells and skin wounds in Example 6.

The results are shown in FIGS. 6A1-A8. Compared with the Vehicle (PBS, control)-treated group, Ot-WHP induces mouse BMDMs to produce chemokines (CXCL1, CXCL2, CXCL3 and CCL2) and cytokines (TNF-α, IL-1β, IL-6 and TGF-β1) in a dose-dependent manner.

Then whether Ot-WHP can induce the production of chemokines and cytokines in the skin wounds of mice was tested. At specified time points (days 0, 0.5, 1, 2, 4, and 6), the wound tissue of the mice was removed and homogenized with 0.1 M PBS (containing 1 mM PMSF, 1 mL/g tissue) in a glass homogenizer. After the homogenization, the homogenate was centrifuged at 12000×g and 4° C. for 30 min. The supernatant was collected, and the chemokines (CXCL1 and CCL2) and cytokines (including TNF-α and TGF-β1) were determined.

The results are shown in FIGS. 6B1-B4. Compared with the Vehicle (PBS, control)-treated group, Ot-WHP can effectively induce the production of chemokines (CXCL1 and CCL2) and cytokines (TNF-α and TGF-β1) in skin wounds of mice.

EXAMPLE 7

Ot-WHP Can Activate MAPKs, NF-κB, TGF-β/Smad Signaling Pathways in Mouse Bone Marrow-Derived Macrophages Mouse bone marrow-derived macrophages (BMDMs) were inoculated into a 6-well plate and cultured without serum for 16 h. For the detection of MAPKs and NF-κB, BMDMs were incubated with different concentrations of Ot-WHP (0, 25, 50, 100 µg/mL) for 30 min. For the detection of TGF-β/Smad signaling pathway, BMDMs were incubated with different concentrations of Ot-WHP (0, 25, 50, 100 µg/mL) for 24 h, or BMDMs were incubated with 100 µg/mL Ot-WHP, with or without TGF-β1 antibody.

Figure 7:
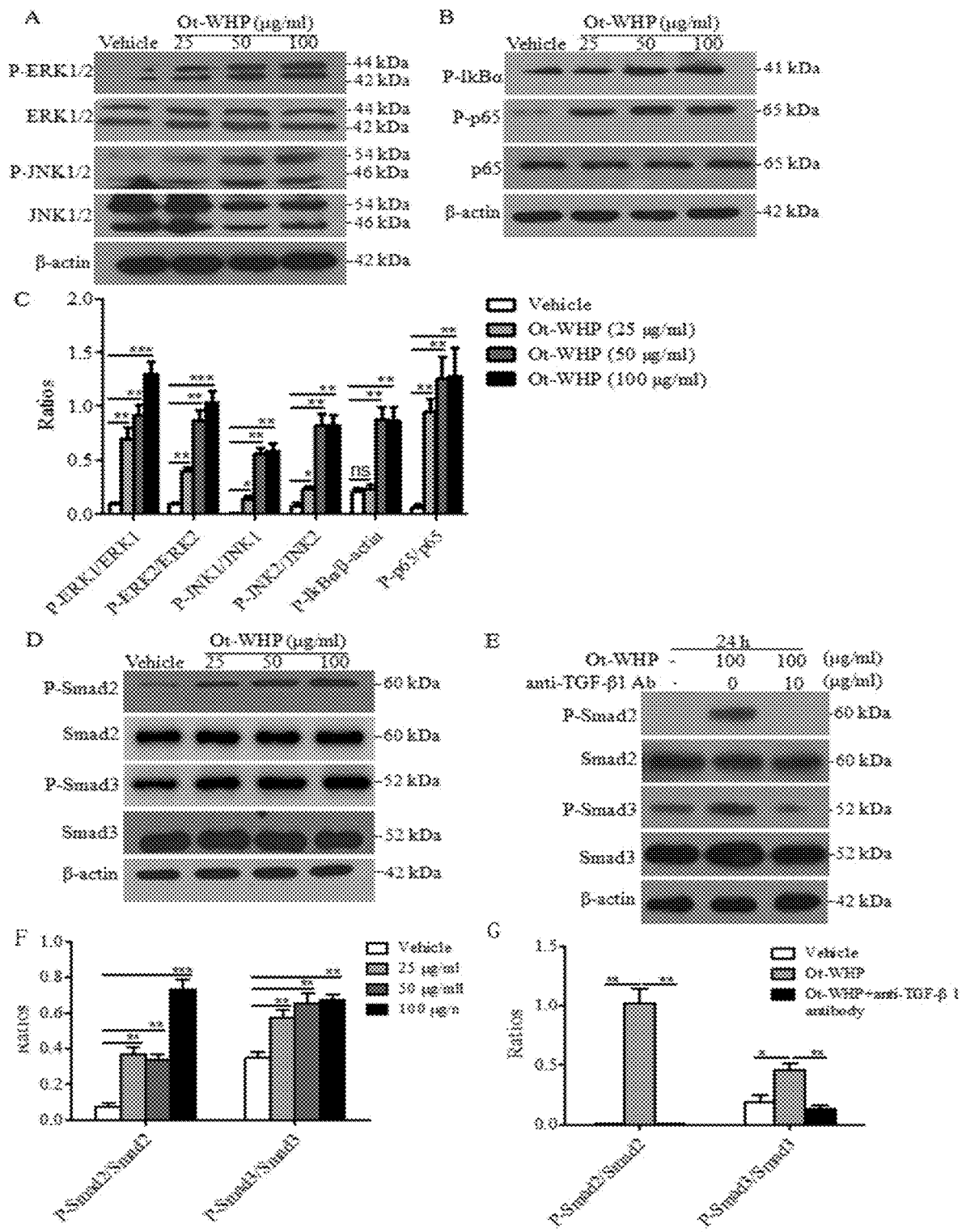
FIG. 7 shows the activation of different signal pathways in mouse BMDMs cells by Ot-WHP at different concentrations in Example 7.

The results are shown in FIG. 7. Compared with the Vehicle (PBS, control)-treated group, Ot-WHP activates the MAPKs (ERK, JNK subunit, FIGS. 7A and 6C), NF-κB (IκBα, p65 subunit, FIGS. 7B and 6C) and Smad (Smad2, Smad3, FIG. 7D) signaling pathways in mouse MAPKs in a dose-dependent manner, where the activation of Smad signaling pathway by Ot-WHP is dependent on the production of TGF-β induced by Ot-WHP (FIGS. 7E -G).

EXAMPLE 8

Ot-WHP Does Not Directly Promote the Proliferation of Keratinocytes and Fibroblasts, But Requires the Coexistence of Macrophages to Promote the Proliferation of Keratinocytes and Fibroblasts Keratinocytes HaCat and mouse fibroblasts ($5 \times 10^3$ cells/well, 100 µL/well) were inoculated into a 96-well plate, and incubated with different concentrations of Ot-WHP (25, 50, and 100 µg/mL). PBS was used as a control. After HaCat was incubated with Ot-WHP for 24 h, and the fibroblasts were incubated with Ot-WHP for 72 h, 10 µl of Cell Counting Kit-8 (CCK-8) solution was added to each well, and incubated for another 2-4 h at 37° C. The absorbency at 450 nm was detected on a microplate reader.

HaCat was co-incubated with THP-1 derived macrophages, and mouse fibroblasts were co-incubated with mouse macrophages BMDMs. HaCat ($1 \times 10^5$ cells/well) or mouse fibroblasts ($1 \times 10^5$ cells/well) were inoculated into a 24-well plate (lower chamber) one day in advance. After adherence, corresponding macrophages ($1 \times 10^5$ cells/well, 100 µL) and different concentrations of Ot-WHP (25, 50, 100 µg/mL) or Vehicle (PBS, control) were added to the co-incubation chamber (upper chamber). After HaCat was co-incubated with THP-1-derived macrophages for 24 h, and the fibroblasts were co-incubated with mouse macrophages BMDMs for 72 h, the co-incubated upper chamber was discarded, and the cell activity in the lower chamber was detected by CCK-8.

Figure 8:
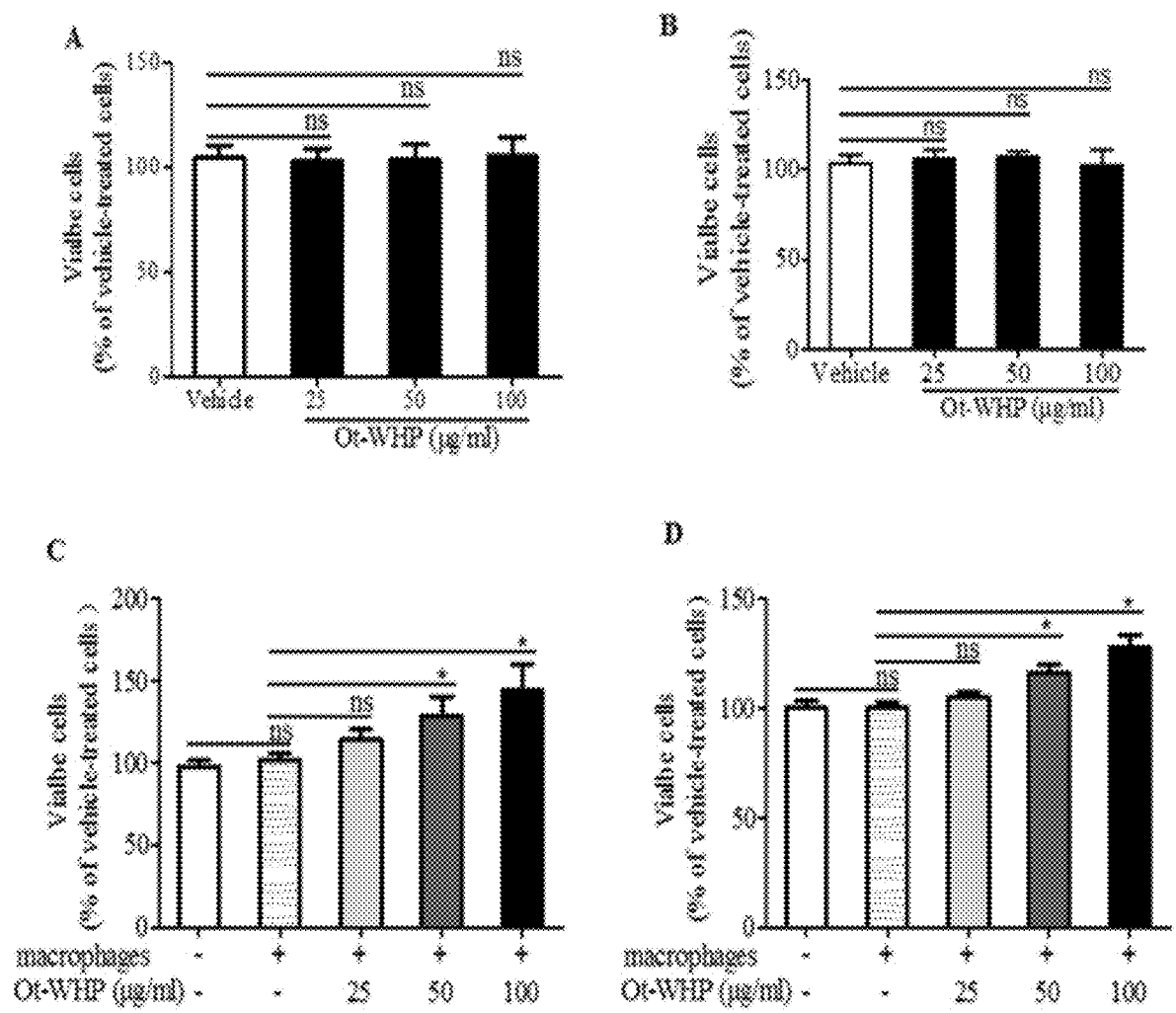
FIG. 8 shows the effect of Ot-WHP at different concentrations on the proliferation of keratinocytes and fibroblasts in Example 8.

The results are shown in FIG. 8. Ot-WHP cannot directly promote the proliferation of keratinocytes (FIG. 8A) and fibroblasts (FIG. 8B). Only when macrophages coexist, Ot-WHP can promote the proliferation of keratinocytes (FIG. 8C) and fibroblasts (FIG. 8D). It shows that Ot-WHP can promote the interaction between macrophages and keratinocytes/fibroblasts.

EXAMPLE 9

Ot-WHP Does Not Directly Promote the Transformation of Fibroblasts into Fibrocytes and Does Not Directly Promote the Collagen Production by Fibroblasts, But Requires the Coexistence of Macrophages to Promote the Transformation of Fibroblasts into Fibrocytes and Promote the Collagen Production by Fibroblasts The method was the same as that in Example 8. The fibroblasts treated in Example 8 were lysed with RIPA cell lysis solution. The protein was extracted, and the expression of α-SMA was detected by Western blot. A higher expression level of α-SMA means a higher transformation of fibroblasts into fibrocytes. The supernatant of the fibroblasts treated in Example 8 was collected, and the production of collagen in the supernatant was quantitatively detected with an ELISA kit.

Figure 9:
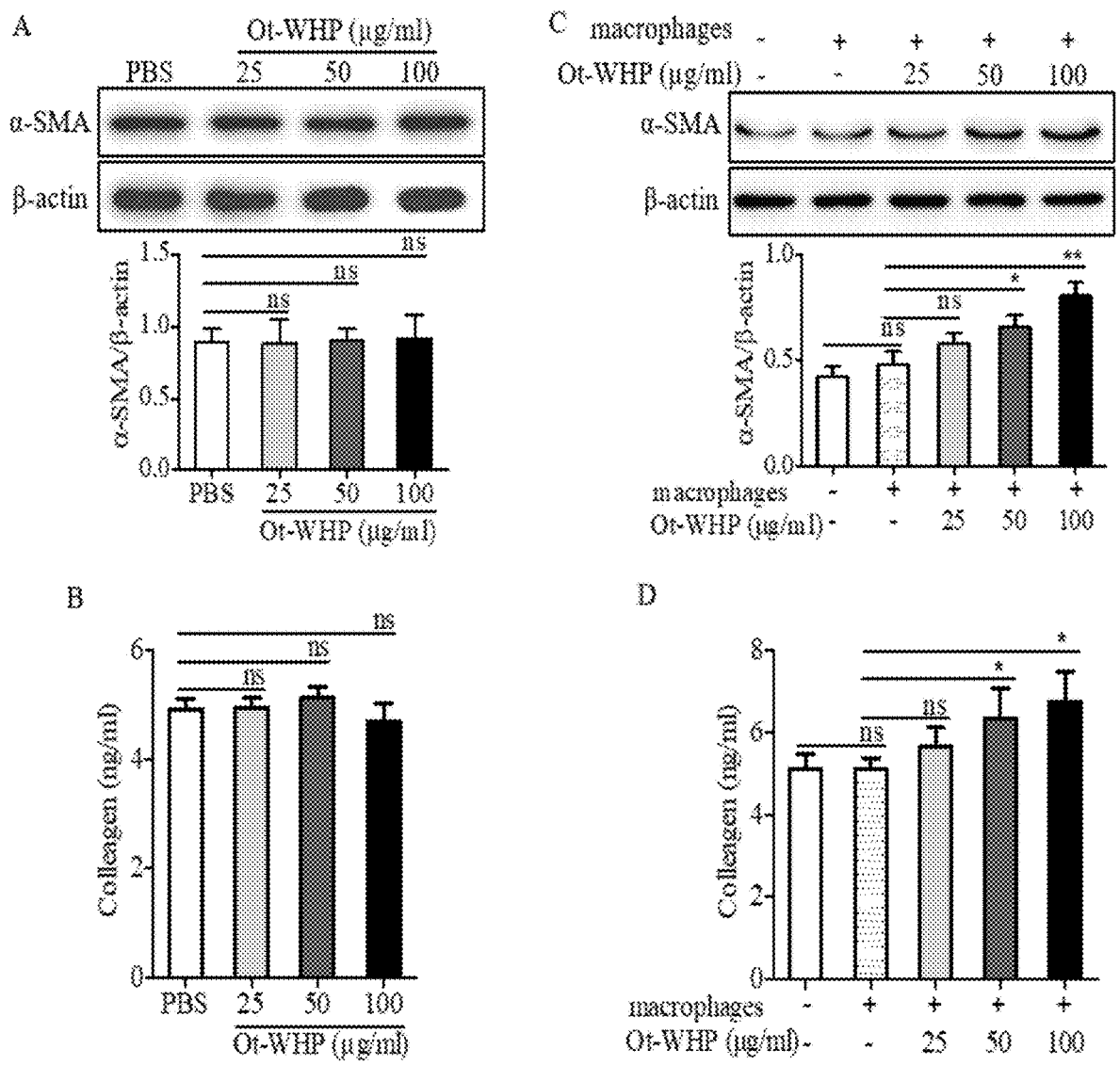
FIG. 9 shows the test results of transformation of fibroblasts into fibrocytes and collagen deposition promoted by different concentrations of Ot-WHP in the presence of macrophages.

The results are shown in FIG. 9. Ot-WHP has no direct effect on the expression of α-SMA in fibroblasts. Ot-WHP does not directly promote the transformation of fibroblasts into fibrocytes (FIG. 9A), and Ot-WHP has no direct effect on the collagen production by fibroblasts and does not directly promote the collagen production by fibroblasts (FIG. 9B). Ot-WHP requires the coexistence of macrophages to promote the expression of α-SMA by fibroblast, that is, promote the transformation of fibroblasts to fibrocytes (FIG. 9C), and promote the collagen production by fibroblasts (FIG. 9D).

While preferred embodiments of the present invention have been described above, the present invention is not limited thereto. It should be appreciated that some improvements and variations can be made by those skilled in the art without departing from the technical principles of the present invention, which are also contemplated to be within the scope of the present invention.

What is claimed is:

1. A drug or a skin care product for promoting skin wound healing comprising an immunomodulating peptide and mouse bone marrow-derived macrophages, the immunomodulating peptide comprising the amino acid sequence as shown in SEQ ID NO: 1;
wherein in the presence of the mouse bone marrow-derive macrophages, the concentration of immunomodulating peptide in the drug or skin care product is 20-100 μg/mL.

2. The drug or a skin care product according to claim 1, wherein the immunomodulating peptide is derived from a concave-eared torrent frog.

3. The drug or a skin care product according to claim 1, wherein the immunomodulating peptide is derived from the skin of concave-eared torrent frog.

4. The drug or skin care product according to claim 1, wherein the drug or skin care product is used to promote the healing of human skin wounds.

5. The drug or skin care product according to claim 1, wherein the drug or skin care product causes the migration of neutrophils and macrophages.

6. The drug or skin care product according to claim 1, wherein the drug or skin care product induces the mouse macrophages and skin wounds to produce chemokines and cytokines.

7. The drug or skin care product according to claim 1 wherein the drug or skin care product activates the MAPKs, NF-κB and TGF-β/Smad signaling pathways in the mouse bone marrow-derived macrophages.

8. The drug or skin care product according to claim 1, wherein in the presence of macrophages, the drug or skin care product promotes the proliferation of keratinocytes and fibroblasts.

* * * * *